United States Patent [19]

Voyt

[11] Patent Number: 4,975,272

[45] Date of Patent: Dec. 4, 1990

[54] METHOD OF AND COMPOSITION FOR THE PREVENTION OF SOLAR RADIATION EXPOSURE-INDUCED FORMATION OF CARCINOGENIC SKIN LIPID DEGRADATION PRODUCTS

[76] Inventor: Walter F. Voyt, 604 E. Palladium Dr., Joliet, Ill. 60435

[21] Appl. No.: 27,416

[22] Filed: Mar. 18, 1987

Related U.S. Application Data

[63] Continuation of Ser. No. 630,336, Jul. 12, 1984, abandoned, which is a continuation of Ser. No. 66,705, Aug. 15, 1979, abandoned, which is a continuation-in-part of Ser. No. 970,060, Dec. 15, 1978, abandoned, which is a continuation of Ser. No. 740,646, Nov. 10, 1976, Pat. No. 4,144,325.

[51] Int. Cl.$^5$ .................... A61K 7/40; A61K 7/42; A61K 7/44; A61K 7/48
[52] U.S. Cl. ............................ 424/59; 424/60; 514/844; 514/847; 514/886; 514/887; 514/937; 514/938
[58] Field of Search .................. 424/59, 60

[56] References Cited

U.S. PATENT DOCUMENTS 4,144,325  3/1979  Voyt ..................... 424/59

FOREIGN PATENT DOCUMENTS 50-13335  5/1975  Japan .................... 424/59

Primary Examiner—Dale R. Ore
Attorney, Agent, or Firm—Neuman, Williams, Anderson & Olsen

[57] ABSTRACT

A method of and composition for the prevention of solar radiation absorption-induced formation of carcinogenic skin lipid degradation products, particularly malonaldehyde, consisting of the application, prior to exposure of the skin to natural or artificial sources of solar radiation, of a composition comprising an ultraviolet screen—effective amount of an ultraviolet absorbing compound selected from the group consisting of a salicylate, a para-aminobenzoate, an alkyl ester of para-dialkylaminobenzoic acid, a benzophenone, a cinnamate, a napthoate, an acid-esterified gallate and mixtures thereof; at least one non-hindered, non-acid esterified, oil soluble, phenolic substituent-bearing latent oxidation inhibitor compound, such as the tocopherols, alcoholic esters of gallic acid, nordihydroguaiaretic acid, and mixtures thereof, the total concentration of said inhibitor present constituting a pro-oxidant-effective amount sufficient to demonstrate pro-oxidant properties, said inhibitor concentration further being insufficient to constitute an ultraviolet screen-effective amount demonstrating ultraviolet screening properties; and an inert carrier vehicle for said compounds comprising an oil soluble component, the vehicle being non-toxic and non-irritating to the skin. Utilization of an oil soluble ultraviolet absorbing compound obviates the necessity for a separate oil soluble component-containing carrier vehicle.

38 Claims, No Drawings

METHOD OF AND COMPOSITION FOR THE PREVENTION OF SOLAR RADIATION EXPOSURE-INDUCED FORMATION OF CARCINOGENIC SKIN LIPID DEGRADATION PRODUCTS

CROSS REFERENCE TO RELATED APPLICATIONS

This application is a continuation of application Ser. No. 630,336 filed on July 12, 1984 (now abandoned), which in turn is a continuation of application Ser. No. 066,705 filed on Aug. 15, 1979 (now abandoned), which in turn is a continuation-in-part of application Ser. No. 970,060 filed on Dec. 15, 1978 (now abandoned), which in turn is a continuation of application Ser. No. 740,646 filed Nov. 10, 1976 (now U.S. Pat. No. 4,144,325).

BACKGROUND OF THE INVENTION

1. Field of the Invention

This invention relates generally to the prevention of solar radiation absorption-induced skin lipid degradation resulting in the formation of carcinogenic products, particularly malonaldehyde, and more particularly relates to a protective composition having ideal properties for such purpose.

2. Description of the Prior Art

Repeated exposure to solar or ultraviolet radiation of lightly pigmented individuals may result in actinic skin—a dry, brown, inelastic, wrinkled skin. Although cosmetically undesirable, actinic skin is not harmful in itself, but is a warning that such conditions as senile keratosis, squamous cell epithelioma, and basal cell epithelioma may develop.

Chronic solar or ultraviolet radiation exposure results in a number of changes in the skin including wrinkling, atrophy, hyper- and hypopigmented macules, telangiectasia, yellow papule and plaque formation, and actinic keratosis. The action spectrum for the induction of some of these conditions in experimental animals by ultraviolet radiation is the same as the action spectrum primarily responsible for solar-induced erythema or sunburn in humans, between 290-320 nm. Some reports indicate that the longer ultraviolet wavelengths between 320-400 nm accentuate the early toxic response to the shorter ultraviolet wavelengths; a mild erythema in humans can also be produced by such radiation.

The role of ultraviolet radiation as a constituent of sunlight in the development of the common human skin cancers, i.e., the basal cell epithelioma, the squamous cell carcinoma, and the much less common malignant melanoma, have been supported by astute observations and epidemiological studies. These various skin cancers are extremely common in susceptible individuals; about 300,000 new cases of skin cancer occur each year. However, investigations confirming this association, as well as the determination of the action spectrum and the required energy levels, have been confined to the aforementioned animal experimentation for practical and ethical reasons.

In addition to animal experimentation, a considerable body of circumstantial evidence supporting the role of ultraviolet radiation, particularly in the form of sunlight, in these three types of skin cancer has been gathered and can be summarized as follows:

(a) Skin cancers do occur predominantly on the sun exposed parts of the body (b) They are more common in regions of the world that receive the most sunlight (c) Pigmented races are much less susceptible to skin cancer formation than Caucasians who work outdoors.

However, the morphological distribution of the most common cutaneous cancer, the basal cell epithelioma, indicates that factors other than ultraviolet radiation must play a role. About one-third of basal cell epitheliomas occur on areas of the skin receiving minimal sun exposure. Therefore, though ultraviolet radiation appears to be a dominant factor in this tumor formation, undetermined factors must participate.

Further, the nature of the chromophore in the skin which absorbs ultraviolet light energy and initiates pathological responses, including erythema, is not known. Proteins containing aromatic amino acids and nucleic acids have been considered likely candidates because of their absorption spectra and the profound effect of ultraviolet energy on these molecules. However, a number of other substances including urocanic acid, melanin, and unsaturated fatty acids of phospholipids have been speculated upon as playing a role in the initial absorption of light energy. It appears as though multiple chromophores are involved in a complex process. Whether this ultraviolet energy absorption leads to the formation of carcinogenic substances has heretofore been the subject of great controversy.

The only practical technique for reducing the pathological effect of ultraviolet radiation in the form of sunlight upon the skin would appear to be to reduce the exposure of skin to solar radiation. This may be accomplished by avoiding exposure of the individual to sunlight. Such limitations do not, however, fit the designs of a civilization which enjoys, or must participate in, outdoor activity, and which further admires melanization of the skin through insolation.

Classically, avoidance of sun exposure did not appear necessary because the effects of sun exposure appeared to be readily mitigated by the topical application of an ultraviolet screening agent. These agents effectively mitigate erythema; no reports are known which indicate how effectively they reduce the other pathological effects of solar radiation in humans. That the known ultraviolet screening products provide such further protection against other non-erythematic effects has recently been assumed by the U.S. Food and Drug Administration, which now allows sellers of consumer sunscreen products to advertise use of their products as a method that "may help prevent premature aging and wrinkling of the skin and skin cancer due to sun overexposure." No experimental verification or other proof of such efficacy in reducing skin cancer has been forthcoming for the extant commercial preparations.

The FDA currently has listed twenty-one dermatologically acceptable sunscreens, which include individual species or mixtures of salicylates, para-aminobenzoates, cinnamates, acid-esterified gallates, napthoates and benzophenones heretofore known to the art, which may be utilized in consumer sunscreen products. Commercial preparations commonly contain these sunscreen compounds together with a cosmetically acceptable carrier and a stabilizer material, e.g., an antioxidant, to protect the oxygen-liable fat and oil ingredients of the preparation, which may include both the sunscreen compounds themselves and components of the carrier material.

Antioxidants or oxidation inhibitor compounds must be used in restricted concentrations to accomplish stabilization of these components against oxidation. This restricted concentration range within which these compounds control or inhibit oxidation is referred to as the antioxidant concentration range and is based on concentration of antioxidant to the fat and oil components; these concentrations are well known to the art. See DeNavarre, *The Chemistry and Manufacture of Cosmetics,* Van Nostrand Company, Inc. (1962), p. 310.

Increasing the amount of oxidation inhibitor compound or antioxidant beyond these values may result in no additional or decreased protection of the oxygen-liable materials. In fact, these compounds actually demonstrate a pro-oxidant effect when used in excess of their antioxidant-effective concentration range. These materials, when present in a pro-oxidant concentration, can be said to be latent oxidation inhibitor compounds. This marked pro-oxidative effect is especially demonstrated by phenolic substituent-bearing latent oxidative inhibitor compounds, including nordihydroguaiaretic acid (NDGA), alcoholic esters of gallic acid, such as propyl gallate, and the pure or mixed alpha, beta, gamma, delta, epsilon, zeta and eta tocopherols.

There is then an art recognized incentive for adding oxidation inhibitor compounds to sunscreen preparations containing the known, FDA approved ultraviolet absorbing compounds only in concentrations within the antioxidant concentration range. The maximum required concentration for phenolic antioxidants in the antioxidant range is about 0.1 wt % based on the fat and oil components of the preparation. For sunscreen preparations containing an evaporative carrier vehicle such as water or alcohols, the fat and oil component content would not exceed about 50 wt % of the preparation. The maximum required phenolic antioxidant concentration based on total product composition therefore would not exceed about 0.05 wt %. For sunscreen preparations that are entirely composed of fatty and oily type materials, the maximum required phenolic antioxidant concentration based on total product composition would not exceed about 0.1 wt %.

In practice, commercial sunscreen preparations generally contain about one-half or less of the maximum useful phenolic antioxidant concentration.

Solar light is an accelerator of oxidation. As consumer sunscreen preparations are frequently exposed to solar radiation prior to application to the skin to control erythema, these preparations are stored in colored containers and wrappers which absorb such radiation. No teachings are extant directed to the use of oxidation inhibitor compounds to stabilize the oxygen-liable materials in these preparations against the effects of ultraviolet light.

Similar teachings are found in the medical and cosmetic arts respecting protection of living human skin from ultraviolet radiation. The application of ultraviolet absorbers or reflectors to the skin during sun exposure is the only recognized technique of protecting that organ from the pathological effect of sunlight. The use of oxidation inhibitor compounds for that purpose has never been taught, and, as noted above, commercial products applied to skin have contained only trace amounts of antioxidants, with but one class of exceptions.

The exception is when the oxidation inhibitor compound also has ultraviolet-absorbing or sunscreen properties. Some phenolic and quinone antioxidants such as hydroquinone and certain gallates have sunscreen properties, and have been employed in commercial sunscreens in concentrations of greater than at least 4% by weight of the total product, a concentration that would result in a minimum acceptable sunscreen effect, i.e., at least an 85% absorption of erythemal ultraviolet light. These products were withdrawn from the market, however, for it was found that the sunscreen-effective concentration was dermatologically unacceptable. For instance, it was shown that three of twelve subjects treated with a hydroquinone sunscreen preparation developed atypical dermatoses, including erythema, dermatitis, and several systemic effects The gallates were similarly shown to be skin irritants.

Similar results leading to withdrawal of other commercial, non-sunscreen cosmetic products utilizing compounds having antioxidant/oxidation inhibitor properties were noted for the tocopherols, such as the Mennen E deodorant products. See *Consumer Reports,* May 1973, pp. 352-53; June 1973, p 371.

These problems were overcome by acid esterification of the phenolic hydroxy (—OH) groups. Such esterification, however, destroyed the antioxidant/oxidation inhibitor properties of these compounds, and, in the case of the tocopherols, destroyed whatever ultraviolet absorbing sunscreen properties demonstrated thereby at those concentrations, which effect was hitherto unknown and is discussed in my issued U.S. Pat. No. 4,144,325. Therefore, it has heretofore been recognized in the art that phenolic and quinone-type oxidation inhibitor compounds are dermatologically unsuitable for use in the concentrations required as the ultraviolet absorbing compound in sunscreen preparations.

No practical value or teaching of use is known, then, for phenolic types of oxiditive inhibitor compounds in sunscreen preparations between the pro-oxidant and sunscreen concentration levels, which correspond to between about 0.1 to 2 wt % of the composition containing said compounds.

Recent reports have been made in the literature about solar ultraviolet-induced lipid peroxidation. Pryor, *Free Radicals in Biology,* Academic Press (1977), pp. 116, 232. Sunlight has been reported to induce the presence of lipoperoxides on the skin, but the significance of the phenomenon has not been recognized. No known reports have been made describing lipid peroxidation of skin lipids treated with the known prior art ultraviolet absorbing sunscreen preparations.

Yet, I have surprisingly found that human skin exposed to solar radiation after treatment with topical applications of known prior art ultraviolet absorbing compound-containing sunscreen preparations, which also contain concentrations of oxidation inhibitor compounds/antioxidants in the antioxidant range, is subjected to skin lipid peroxidation which produces the carcinogenic and skin aging compound malonaldehyde:

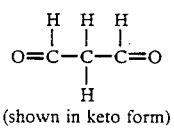

(shown in keto form)

Malonaldehyde is a mutagen, as established by the Ames Salmonella test. Since about 90 per cent of the compounds found mutagenic in the Ames test are also carcinogenic, the probability of malonaldehyde being a human carcinogen is very great. Malignant skin tumors have been reported in rats receiving an effective topical application of 60 μg of malonaldehyde; as a result, malonaldehyde is now considered a potent carcinogen by the scientific community. As it is a water soluble agent, its indigenous formation on and in the skin during sun exposure does not restrict its presence to the skin. It can enter and be carried by the vascular system to all parts of the body. What deleterious effects it has there are unknown, although it has recently been implicated in certain types of heart damage.

Malonaldehyde has also been shown to be a dangerous cross linking agent capable of in vivo cross linking with the primary amino groups of proteins, nucleic acids and their bases, or phospholipids. Cross linking of skin proteins, especially collagen, is widely thought to be a mechanism of both normal and premature skin aging.

The presence of malonaldehyde on the skin during sun exposure thus offers a plausible explanation for the etiology of both skin cancers and premature wrinkling and aging of the skin caused by excessive sun exposure.

Generally, all commercial sunscreen preparations which I have tested do not reduce solar radiation absorption-induced malonaldehyde formation from skin epithelial tissue more than about 50% of the concentration that would have developed in the absence of application of the sunscreen. The majority of the most effective sunscreens known to the art, even when combined with an antioxidant in the antioxidant range, reduce malonaldehyde by much less than 50% when applied to the skin exposed to sunlight.

More troubling is that my testing showed that use of several consumer sunscreen products actually increased the amount of malonaldehyde formed over that which would have developed in the absence of the sunscreen applied.

Since there is no known effect threshold value for human carcinogens, any concentration of a carcinogen in or on the body is dangerous. It is known that exposure to a higher concentration of a carcinogen is more dangerous than a lower concentration. Therefore, any reduction in exposure to a carcinogen, especially reduction to zero or near zero exposure, is highly desirable.

None of the known, most widely used and effective ultraviolet absorbing compound-containing sunscreens known to the art, e.g., those containing salicylates, para-aminobenzoates, cinnamates, acid-esterified gallates, napthoates and benzophenones, therefore, provide the critical property of preventing pathological and carcinogenic chemicals such as malonaldehyde from forming on the skin during exposure to solar radiation while reducing erythema.

SUMMARY OF THE INVENTION

The present invention relates to a method of and composition for the prevention of solar radiation absorption-induced formation of carcinogenic skin lipid degradation products, particularly malonaldehyde. The method consists of the application, prior to exposure of the skin to natural or artificial sources of solar radiation, of a dermatologically acceptable protective composition comprising an ultraviolet screen-effective amount of an ultraviolet absorbing compound selected from the group consisting of a salicylate, a paraaminobenzoate, an alkyl ester of para-dialkylaminobenzoic acid, a benzophenone, a cinnamate, a napthoate, an acid-esterified gallate and mixtures thereof; and at least one non-hindered, non-acid esterified, oil soluble phenolic substituent-bearing latent oxidation inhibitor compound, the total concentration of said inhibitor present constituting a pro-oxidant-effective amount sufficient to demonstrate pro-oxidant properties, said inhibitor concentration further being insufficient to constitute an ultraviolet screen-effective amount demonstrating ultraviolet screening properties admixed in an inert carrier vehicle comprising an oil soluble component, which is inert, non-toxic, and non-irritating to the skin. The necessity for use of an oil soluble component-containing carrier vehicle, however, may be obviated by using an oil soluble ultraviolet absorbing compound of said group.

The present invention overcomes the drawbacks of the prior art compositions by providing a method of and composition for simultaneously reducing erythema of the skin and substantially completely preventing the formation of carcinogenic and skin aging skin lipid degradation products on the skin, notably malonaldehyde, resulting from exposure of the skin to solar radiation, including radiation such as ultraviolet radiation, which comprises a part or constituent of the solar radiation energy spectrum. The composition further possesses good resistance to chemical and photochemical changes in composition which might decrease its sunscreen and skin lipid degradation product formation prevention properties, is not easily absorbed through the skin, causes no irritation, sensitization or other tropic changes in the skin, forms a continuous film when applied to the skin, and is compatible with all acceptable cosmetic vehicles.

Accordingly, it is an object of this invention to provide an improved method for preventing skin cancer and skin-aging caused by the formation and presence of skin lipid degradation products, particularly malonaldehyde, on the skin while reducing erythema of the skin caused by exposure to solar radiation.

It is a further object of this invention to provide a composition which simultaneously prevents erythema of the skin while substantially preventing the formation of carcinogenic chemicals and skin aging skin lipid degradation products on the skin during solar radiation exposure.

It is another object of this invention to provide sunscreen and latent oxidation inhibitor compound-containing compositions with greater efficacy in reducing the formation of carcinogenic and skin aging skin lipid degradation products on the skin than achievable with dermatologically acceptable prior art sunscreens, even when combined with antioxidant amounts of oxidation inhibitor compounds.

It is a further object of this invention to provide a sunscreen and latent oxidation inhibitor compound-containing composition which contains less sunscreen than formerly utilized in sunscreen compositions to achieve substantially complete prevention of the formation of carcinogenic and skin aging skin lipid degradation products on the skin during solar radiation exposure of the skin.

It is yet another object of this invention to provide a sunscreen and latent oxidation inhibitor compound-containing composition which simultaneously reduces erythema and substantially completely prevents the formation of carcinogenic and skin aging skin lipid degradation products on the skin during solar radiation exposure while concomitantly permitting tanning of the skin, by employing less sunscreen than formerly utilized to reduce erythema in commercial ultraviolet absorbing sunscreen compositions.

It is a further object of this invention to provide a sunscreen and latent oxidation inhibitor compound-containing composition which simultaneously reduces erythema and substantially completely prevents the formation of skin aging skin lipid degradation products on the skin during solar radiation exposure while concomitantly reducing the irritation and sensitization of the skin caused by the sunscreen by employing less sunscreen than formerly utilized to reduce erythema in commercial ultraviolet absorbing sunscreen compositions, and by employing oil soluble latent oxidation inhibitor compounds dissolved in oily primary or secondary vehicles.

It is another object of this invention to provide a composition for simultaneously reducing erythema of the skin and substantially preventing the formation of carcinogenic and skin-aging skin lipid degradation products resulting from exposure of the skin to solar radiation which possesses good resistance to chemical and photochemical changes in composition, which decreases its sunscreen and skin lipid degradation product formation prevention properties, is not easily absorbed through the skin, causes no irritation, sensitization or other tropic changes in the skin, forms a continuous film when applied to the skin, and is compatible with all acceptable cosmetic vehicles.

Other objects and advantages of this invention will become apparent upon reading the following detailed description and appended claims.

DESCRIPTION OF THE PREFERRED EMBODIMENT

The preferred method of the invention provides for the prevention of solar radiation absorption-induced formation of carcinogenic skin lipid degradation products, particularly malonaldehyde, by the application, prior to exposure of the skin to natural or artificial sources of solar radiation, of a protective composition comprising an ultraviolet screen-effective amount of an ultraviolet absorbing compound selected from the group consisting of a salicylate, a paraaminobenzoate, an alkyl ester of para-dialkylaminobenzoic acid, a benzophenone, a cinnamate, a napthoate, an acid-esterified gallate and mixtures thereof, and at least one non-hindered, non-acid esterfied, oil soluble, phenolic substituent-bearing latent oxidation inhibitor compound, such as the tocopherols, alcohol esters of gallic acid, such as propyl gallate and nordihydroguaiaretic acid (NDGA) and mixtures thereof, the total concentration of said inhibitor present constituting a pro-oxidant-effective amount sufficient to demonstrate pro-oxidant properties, said inhibitor concentration further being insufficient to constitute an ultraviolet screen-effective amount demonstrating ultraviolet screening properties.

The particularly preferred ultraviolet-absorbing compounds for use in the composition of the invention are the alcohol and oil soluble, dermatologically effective erythemal range ultraviolet absorbing salicylates, such as menthyl or homomenthyl salicylate (homosalate), the paraaminobenzoates and alkyl esters of para-dialkylaminobenzoic acid, such as glyceryl p-aminobenzoate, isoamyl N, N-p-dimethylaminobenzoate, and amyl p-dimethyl aminobenzoate, including those alkyl esters of paradimethylaminobenzoic acid disclosed in Kreps U.S. Pat. No. 3,403,207, the benzophenones, the napthoates, the acid-esterified gallates, and the cinnamates, such as 2-ethoxyethyl-p-methoxycinnamate, and mixtures thereof.

These particularly preferred ultraviolet absorbing compounds include those materials recognized by the Food and Drug Administration as safe and effective sunscreens: aminobenzoic acid; cinoxate; diethanolamine para-methoxycinnamate; digalloyl trioleate; dioxybenzone; ethyl 4-[bis (hydroxypropyl)] aminobenzoate; 2-ethylhexyl-2-cyano-3,3-diphenylacrylate; ethylhexyl-para-methoxycinnamate; 2-ethylhexyl salicylate; glyceryl aminobenzoate; homosalate; lawsone with dihydroxyacetone, menthyl anthranilate; oxybenzone Padimate A (amyl para-dimethylaminobenzoate); Padimate O (octyl dimethyl para-aminobenzoate); 2-phenyl-benzimidazole-5-sulfonic acid; red petrolatum; sulisobenzone; titanium dioxide, and triethanolamine salicylate.

Other preferred ultraviolet absorbing compounds include 2-ethylhexyl-4-phenylbenzophenone-2'-carboxylic acid; 3-(4-methylbenzylidene)-camphor; sodium 3,4-dimethylphenyl-glyoxylate; allantoin combined with aminobenzoic acid; 5-(3,3-dimethyl-2-norbornyliden) 3-penten-2-one; and dipropylene glycol salicylate.

These ultraviolet absorbing compounds demonstrate oil or alcohol solubility, and are therefore compatible with the oil soluble latent oxidation inhibitor compounds utilized in the protective composition. These compounds additionally resist topical loss after administration from perspiration and swimming.

The optimum ultraviolet absorbing compounds for use in the composition of the invention are the derivates of vitamin Bx active para-aminobenzoic acid: the alkyl esters of para-aminobenzoic, para-alkylaminobenzoic, and paradialkylaminobenzoic acid, such as the amyl, hexyl and octyl para-dimethylaminobenzoates disclosed in Kreps U.S. Pat. No. 3,403,207, e.g., Padimate-A(amyl para-dimethylaminobenzoate), and Padimate-O(octyl dimethyl para-aminobenzoate). These compounds have good oil solubility, strong absorptivities, proper erythemal energy absorption spectra, low toxicity, and are limpid, low viscosity fluids which can serve as all, or a substantial portion of, a secondary carrier component for the oil soluble latent oxidation inhibitor compounds of the composition when the composition contains a primary evaporative component, such as in lotions or alcoholic preparations, or as a primary or sole carrier vehicle for said oxidation inhibitor compounds, so as to obviate the need for an oil soluble component-containing carrier vehicle.

The ultraviolet-absorbing compounds used in the protective composition of the invention must be present in a concentration that provides at least an 85% reduction of incident erythemal radiation. Representative quantities necessary in the composition are as follows:

| Sunscreen | Weight percentage of screen necessary to provide 7% erythemal transmission |
|---|---|
| Glyceryl p-aminobenzoate | 2.0 |
| Isoamyl N,N-p-dimethyl aminobenzoate | 1.3 |
| Homomenthyl salicylate | 11.0 |
| 2-ethoxyethyl-p-methoxycinnamate | 1.4 |
| 2-ethylhexyl-p-dimethylaminobenzoate | 1.3 |

Necessary concentrations of the other ultraviolet absorbing compounds useful in the protective composition of this invention may be readily determined by one skilled in the sunscreen art.

The particularly preferred non-hindered, non-acid esterified, oil soluble, phenolic substituent-bearing latent oxidation inhibitor compounds are the monomethyl, dimethyl or trimethyl derivates of tocol having the following formula:

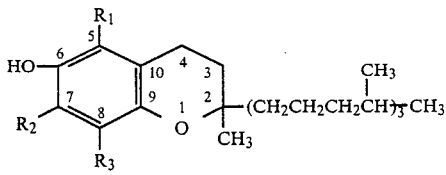

wherein $R_1$, $R_2$ and $R_3$ are selected from the group consisting of hydrogen and methyl, at least one of said substituents being a methyl group, alone or in combination, such compounds being denominated as follows:

| | |
|---|---|
| alpha tocopherol | 5,7,8-trimethyl tocol |
| beta tocopherol | 5,8-dimethyl tocol |
| gamma tocopherol | 7,8-dimethyl tocol |
| delta tocopherol | 8-methyl tocol |
| epsilon tocopherol | 5-methyl tocol |
| zeta tocopherol | 5,7-dimethyl tocol |
| eta tocopherol | 7-methyl tocol |

While it has heretofore been known that tocopherols are primary in vivo lipid antioxidants, I have found that oral administration of 200 I.U. per day of d-alpha tocopherol derived from d-alpha tocopherol succinate prior to, and during, an solar radiation exposure testing period, plus an additional 30 I.U. per day from normal nutrition, did not noticeably delay rapid malonaldehyde formation on the test subject's skin during sun exposure. It was surprising then that known and art taught methods of surpressing oxidation of lipids with concomitant malonaldehyde formation by ingestion of natural tocopherol antioxidants was ineffective for solar radiation exposed skin, while topical application of a pro-oxidant concentration of the same compounds was extremely effective. It is all the more surprising in view of the work of reputable consumer groups, such as Consumer Union, who had systematically gathered all scientific work done on evaluation of topically applied vitamin E active materials, and after carefully considering this body of information, had concluded that "there is absolutely no evidence that vitamin E applied to the skin is in any way beneficial to that organ."

Not only are the tocopherols physiologically preferred because of their vitamin E properties, but they also have excellent solubility in oil and alcohol vehicles and ultraviolet absorbing sunscreen compounds, show no short-term chemical or photochemical change in structure which would decrease their malonaldehyde-reducing properties, are not easily absorbed through the skin, cause no irritation or other tropic changes in the skin when used in the proper concentration and vehicle, are insoluble in water and Perspiration, are liquids that form a continuous film when applied to the skin, and exhibit no residual staining to skin or clothing. The tocopherols show consistent performance for malonaldehyde reduction in all types of common vehicles including alcohol and oils.

Other antioxidants which are structurally and functionally related to the tocopherols have also been found to be effective in significantly reducing malonaldehyde formation on solar radiation-exposed skin. These related compounds are represented by gallic acid, NDGA and their alcoholic esters, such as propyl gallate, octyl and dodecyl. These compounds, however, are not primary in vivo lipid antioxidants like the tocopherols, and are less physiological acceptable for that reason. Yet these two additional antioxidants have a low order of toxicity, and well represent latent oxidation inhibitor compounds other than the tocopherols which are effective for the purpose of this invention.

There are four distinguishing features of the latent oxidation inhibitor compounds which effectively reduce malonaldehyde and are useful in the composition of the invention: such compounds are (1) non-hindered, (2) phenolics, (3) that have not been acid esterified, and (4) have good oil solubility. All four of these criteria must be met for inhibitor compounds useful in this invention.

First, "non-hindered" indicates that there is no steric hindrance of the latent oxidation inhibitor compound's phenolic group. Therefore, no group larger than an ethyl group may be positioned adjacent to the functional hydroxy group. BHT is an example of a hindered phenol that would not be useful since it contains bulky tert butyl group adjacent to the functional hydroxy substituent.

Secondly, the effective compounds are of the phenolic type, e.g., bearing phenolic groups or substituents. These compounds contain one or more of the phenolic hydroxy groups that are responsible for the latent oxidation inhibitor properties of the compound. Antioxidants/oxidation inhibitors with sulfur or nitrogen functional groups are as a group less effective than the phenolic types.

Thirdly, the phenolic hydroxy group which is responsible for the compound's latent oxidation inhibitor properties must not be destroyed by acid esterification; acid esterification of tocopherols and gallates renders these compounds useless as oxidation inhibitors. It should be noted that alcoholic esterification of acid groups on the molecule is permissible, as alcoholic esterification does not destroy the functional hydroxy groups. Therefore, for example, alcoholic esters of the gallates are operable latent oxidation inhibitor compounds, such as propyl gallate, in the composition of this invention, but acid esters, such as the galloyl propinates, are not. Digalloyl trioleate, which comprises an FDA-approved sunscreen, is an acid ester of a condensed gallate, but is not a latent oxidation inhibitor compound of this invention.

Fourthly, the latent oxidation inhibitor compounds must have sufficient solubility in oils and fats, i.e., they must be at least about 0.2 wt % soluble in commonly-used carrier vehicle oils such as vegetable oils and petrolatums. Effective latent oxidation inhibitor compounds with lesser oil solubility are of value when combined with other effective compounds in a mixture, and the mixture of compounds as a whole meets these minimum oil solubility requirements. The oil solubility requirements must also be met so as to insure that the oxidation inhibitor compound is not dissolved out of the oil when applied to the skin by perspiration on the skin, which would result in skin irritation and reduced effectiveness.

Any other compound demonstrating antioxidant properties with water solubility in excess of about 0.5 wt % will not be effective for the purpose of the invention unless it is a recognized synergist for an oil-soluble, effective latent oxidation inhibitor compound, i.e., ascorbates for tocopherols. Water soluble oxidation inhibitor compounds will not dissolve sufficiently in skin lipids to prevent skin lipid peroxidation with concomitant malonaldehyde formation. Therefore, even though the other three requirements are meet, a lack of proper oil solubility renders otherwise effective oxidation inhibitor compounds such as hydroquinone useless in the composition of this invention.

The oil solubility of the latent oxidation inhibitor compounds is critical in both evaporative and non-evaporative carrier vehicles An evaporative carrier comprises a primary, evaporative component and a secondary, non-evaporative component, while a non-evaporative carrier comprises only a single, primary non-evaporative component, similar to the secondary component in an evaporative carrier. The primary component usually makes up about 50 wt % or more of the carrier vehicle. When the primary component is comprised of non-evaporative oily and fatty materials, it serves as a carrier for the active compounds (sunscreen and oil-soluble latent oxidation inhibitor) both in storage and after application to the skin. However, when the primary component is an alcohol or water, it serves as a carrier of the active compounds only in a container and immediately upon application to the skin; after application, the primary component is rapidly lost by evaporation and/or skin absorption. The secondary or non-evaporative component of the carrier does not rapidly evaporate or become absorbed by the skin on application, however, and remains to serve as the carrier for the active compounds after evaporation of the primary component.

The lower effective concentration limit of the effective latent oxidation inhibitor compounds is about 0.1 wt % based on total composition for all compounds tested, provided they are contained in a primary evaporative component such as alcohol in a preparation having an evaporative carrier vehicle. Such preparations, as just noted, must contain a non-evaporative component which serves as the secondary carrier for the inhibitor compounds after the volatile portion has evaporated after application to the skin. This secondary component, which may be considered as the residue left behind after evaporation of the primary vehicle, must be an oily material such as an oily sunscreen, saturated vegetable fat or a petrolatum or mixture of these materials, and must be present at a minimum of about 5 wt % of the preparation, and preferably 10 wt % or more of the preparation.

Again, as noted above, it is essential that the effective latent oxidation inhibitor compounds are soluble in the secondary component on the skin after the evaporative portion has evaporated. The oil solubility of the individual effective inhibitor compounds or mixtures of compounds must be at least 2 wt % in the secondary component when the minimum amounts of oxidation inhibitor compounds and secondary component are used for the invention.

When the protective composition contains only a non-evaporative carrier vehicle such as a saturated vegetable oil or petrolatum, the lower concentration limit for the oxidation inhibitor compounds is about 0.2 wt %.

When mixtures of the latent oxidation inhibitor compounds are employed, one or more of such compounds may be present in a concentration within the antioxidant range, e.g., below the latent oxidation inhibitor concentration level for that compound. The sum of the concentrations of such compounds present, such as a combination of a tocopherol and an alcoholic ester of gallic acid, however, must meet or exceed the minimum latent oxidation inhibitor concentration set out above for use of a single latent oxidation inhibitor compound.

The lower effective concentration limit of the effective latent oxidation inhibitor compounds may also be stated as percentages based on fat and oil content of the preparation. For instance, the minimum required concentration of effective antioxidant to fat and oil content is from 0.2 to 2 wt % for primary evaporative-based preparations. In these preparations, the fat and oil content, which fats and oils comprise the secondary vehicle, may vary from about 5 to about 50 wt %; the minimum based on that content is thus:

$$\frac{0.1\%}{5\%} \text{ to } \frac{0.1\%}{50\%} = 2\% \text{ to } 0.2 \text{ wt }\%$$

For compositions that are entirely oily or fatty based, the minimum required concentration on the basis of said oil or fat content is about 0 2 wt %. The minimum required concentration for all compositions of the invention, then, of latent oxidation inhibitor compound to the fat and oil content is about 0.2 wt %, but can extend to 2 wt % for compositions containing a primary evaporative base.

The upper limit concentration is set by the maximum concentration which will not cause sensitization and other dermatological problems on the skin by users of the protective composition of the invention. Numerous examples of commercial products containing phenolic and quinone antioxidant compounds intended for application t the skin show that, in concentrations of only 0.05 wt %, when not dissolved in an oily vehicle, such compounds will cause skin sensitization and other dermatological problems. Dissolving these compounds in an oily vehicle, especially petrolatum, reduces the dermatological problems until an upper concentration limit of about 2 wt % is reached.

The upper concentration limit for the latent oxidation inhibitor compounds in the protective compositions of this invention is thus 2 wt % based on total composition weight. The concentration range of from about 0.1 to 2 wt % of these compounds results in the demonstration of pro-oxidant properties without any erythema-preventing ultraviolet screen or absorption effectiveness: it has been well established that the concentration of a sunscreen must be sufficient to absorb at least 85% of the incident solar erythemal radiation when applied in a thin film to the skin, and in this concentration range the oxidation inhibitor compounds of this invention will not significantly delay erythema following sun exposure.

A major benefit from the composition and method of the invention is a reduction in the amount of ultraviolet absorbing sunscreen compound necessary to accomplish the intended purpose of the protective composition. When used alone, sunscreens must absorb about 99% of the incident solar erythemal radiation to satisfactorily reduce solar-induced carcinogenisis and premature skin wrinkling. The sunscreen concentration must be very high for this effect. Such use of sunscreens in high concentration ranges frequently lead to dermatological problems, yet, this was the price that previously had to be paid for reduction of these pathological conditions.

The compositions of the invention allow reduction of the concentration of ultraviolet absorbing compound necessary for these purposes, with a concomitant reduction in dermatological problems. For instance, when a consumer desires to reduce skin aging and cancer from ultraviolet radiation or sun exposure by reducing the amount of skin lipid oxidation products formed on his skin, and is not particularly concerned with maximum erythema reduction, he may choose the composition of the invention that contains less sunscreen than necessary to absorb 99% of solar erythemal energy and enjoy the desired malonaldehyde reduction, as a major sunscreen effect is not required for the composition and method of the invention in order to reduce these undesirable conditions of the skin caused by malonaldehyde formation. This nondependence on sunscreen compounds to reduce the pathological conditions caused by skin lipid oxidation followed by the presence of malonaldehyde on the skin also affords the further benefits of simultaneous reduction of erythema, skin irritation, and malonaldehyde formation with tanning of the skin.

As the latent oxidation inhibitor compounds present in the composition of the invention demonstrate pro-oxidative properties, they will require stabilization in many types of formulations. Many known antioxidant compounds may be used for this purpose in an antioxidant concentration, including butylated hydroxytoluene (BHT) butylated hydroxyanisole (BHA) and the like. When the latent oxidation inhibitor compound is a tocopherol or mixture thereof, additional stabilizers may also be incorporated to increase their life with respect to exposure to metal salts, particularly ferric salts. Metal chelating agents which constitute antioxidant synergists are particularly useful and may be incorporated in the composition of the invention. Such agents include triethanol amine and its fatty acid salts, isopropylamine and its fatty acid salts, ethylenediaminetetraacetic acid and its disodium salt, citric acid, its salts and its fatty acid esters, ascorbic acid, its salts and its fatty acid esters, phosphoric acid, its salts and its fatty acid esters, and the like.

Additional stabilizer compounds useful in the composition of the invention include dilauryl thiodipropionate, 4-hydroxymethyl-2, 6-di-tert butylphenol, thiodiproprionic acid, 2, 4, 5-trihydroxybutyrophenone, 2, 5-di-tert-butylquinol, N, N'-diphenyl-p-phenylenediamine, and 6-ethoxy-1, 2-dihydro-2, 2, 4-trimethylquinoline, alone or in combination. When used as stabilizers these antioxidant-synergists would not be present in a concentration exceeding 0.05 wt %, except the ascorbates, which may be present up to 0.5 wt %. Combinations of both oil and water soluble stabilizer-synergists may also be utilized effectively e.g., an ascorbate with BHT or BHA.

Other antioxidants which stabilize or work synergistically with the latent oxidation inhibitor compounds, particularly the tocopherols, may also be present in the composition. The ascorbates and their salts and esters are particularly preferred synergists because of their low toxicity and well-known strong synergism with tocopherols. Ascorbates do not appreciably prevent malonaldehyde formation from skin exposed to solar radiation, as they do not prevent skin lipid peroxidation, but they appear to have some activity in reducing already formed malonaldehyde to less toxic substances.

The primary and any secondary carrier vehicles of the protective compositions must be inert, stable, and nontoxic, such that they do not hasten destruction of the latent oxidation inhibitor compounds. Both carrier vehicles as a whole should not be such that would readily form free radicals by themselves or in the presence of air and sunlight, free radicals being known destroyers of phenolic oxidation inhibitor compounds. The primary vehicle of the invention should be limited to water, alcohols, silicone oils, petrolatums, waxes, and stable vegetable oils, alone or as mixtures. The secondary vehicle of the invention should be limited to silicone oils, oily sunscreens, petrolatums, waxes, and oxygen-stable vegetable oils, alone or as mixtures.

Antimicrobial agents may also be included in the composition of the invention to reduce the growth of bacteria, molds, fungi and the like The alkyl parabens are the preferred antimicrobials for incorporation into the composition of the invention, particularly methyl and propyl paraben.

Additional components well known to the cosmetic art may also be incorporated in the composition of the invention, such as extending components, emollients such as lanolin and its derivatives, emulsifiers, perfumes and coloring agents.

The method of this invention also insures inhibition of carcinogenic nitrosamine formation on the skin during solar radiation exposure when the latent oxidation inhibitor compound is a tocopherol or mixture of tocopherols. Although nitrosamine formation has not been demonstrated, as yet, on the skin during solar radiation exposure, the skin normally contains a number of nitrogen compounds, including urea, ammonia, and amino acids, capable of nitrosamine formation during sun exposure. Tocopherols inhibit nitrosamine formation, and would prevent their formation on the skin during such exposure when the method of the invention is practiced.

The following examples illustrate the method and compositions of the invention.

GENERAL EXPERIMENTAL PROCEDURE

The following general procedure was used in investigating skin lipid peroxidation with accompanying evolution of the carcinogen malonaldehyde on exposure to solar radiation.

Part 1

A rectangular strip of paper approximately $14 \times 44$ mm (1 in.$^2$) was cut from Whatman No. 5 filter paper. The strip was approximately 0.17 mm thick and weighed about 50 mg. The tare weight of the filter paper was taken. The filter paper was then used to take a skin lipid sample.

Skin lipid samples were taken from an adult male subject. This subject had a history of normal response to solar erythema and tanning. The subject had normal oily skin that is lightly pigmented when untanned. The subject was maintained on a normal diet prior to and during the test period. The diet was supplemented with 200 I U per day of d-alpha tocopherol succinate for three months prior to and during the test period.

Skin lipid samples were taken from the clean untanned face of the subject by pressing the filter paper strip very firmly against the skin of the face. While continuing the pressure, the strip was moved along the surface of the face. Sufficient pressure was applied to the face to insure that both surface lipids and a significant amount of epithelial tissue was collected on the paper strip.

Generally, one paper strip was used to remove skin lipids and epithelial cells from an area of one half of the face. If two samples were taken, the second paper strip was used as described to remove skin samples from the remaining half of the face. If three samples were taken, each paper strip was used to remove a skin sample from one-third of the face.

The weight of the skin lipids and epithelial cells collected on the paper strip(s) was obtained by weighing the Paper strip(s) and sample and subtracting the tare weight of the Paper strip(s).

If the Paper strip received a topical application of an experimental preparation, the preparation was applied uniformly on the skin sample side of the paper strip with a 50 $\mu$l syringe. The treated strip was then held for about 15 minutes before proceeding to Part 2 of the procedure.

It is important to note that all preparations of the following experiments were allowed to set on the skin samples 15–20 minutes before solar radiation exposure. This is in fact an important step in the actual use of the novel compositions of the invention, as this short waiting time before solar radiation exposure greatly improves their performance. This time is required to allow the latent oxidation inhibitor compounds to diffuse to the skin samples in these experiments, and, in actual use, to allow similar diffusion on the skin.

Part 2

The paper strip from Part 1 was placed inside a pure quartz (fused silica) spectrophotometric cell. The cell had a path length of 1 cm., a height of 5 cm. and a volume of 5 ml. The paper strip was pushed forward so that the side of the paper with the sample was in contact with the inner window of the cell.

One-half ml of purified, deionized water (pH=7.0) was pipetted into the cell. The cell was then sealed with a Teflon stopper. The water inside the cell slowly moistened the paper strip by capillary action. The bulk of the water remained at the bottom of the cell and was not in contact with the sample on the paper strip.

The silica cell was labeled to identify the sample.

Samples that were exposed to ultraviolet radiation in the form of sunlight were taken outdoors and placed on a 45° angled support so the side of the cell with the sample faced the sun at a 45° angle. If more than one sample was to be exposed to sunlight, the multiple samples were exposed to sunlight simultaneously at adjacent locations on the cell supporter. A control sample that was not exposed to sunlight was simultaneously placed in a dark location indoors.

After the exposure period, the cell was brought to the laboratory bench and uncapped. One and one-half ml. of deionized water was added to the cell. After recapping the cell was shaken vigorously for one minute. The aqueous layer was now ready for analysis by the thiobarbituric acid (TBA) test.

Part 3

The aqueous layer from the silica cell was poured into a 35 ml test tube. One ml of a 20% (wt/v) trichloroacetic acid solution was pipetted into the test tube. Then 2 ml of a 0.67% (wt/v) 2-thiobarbituric solution was pipetted into the test tube.

The test tube was placed in a boiling water bath for ten minutes. The tube was then placed in a cool water bath until it reached ambient temperature.

The sample was then vacuum filtered to remove suspended matter by using a pre-washed Gelman Type A-E 100% pure fiber glass filter.

The filtrate was placed in a 1 cm silica cell and the absorbance of the sample was measured at 532 nm with a Beckman DU-2 spectrophotometer using water as a blank.

Sample absorbance was converted to $\mu$g/ml of malonaldehyde by comparing the sample absorbance against the absorbance of a malonaldehyde calibration curve prepared from pure malonaldehyde bis (dimethyl acetal) (from Aldrich Chemical Company, Inc.). Spectrophotometric conditions for preparation of the malonaldehyde calibration curve were identical to those used in determining the absorbance of the sample.

The quantity of malonaldehyde present was calculated as follows:

M = $\mu$g malonaldehyde/5 ml of aqueous sample volume, = 5 ml × A, where

A = $\mu$g/ml of malonaldehyde in the aqueous sample as determined from the calibration curve.

The TBA number of the skin sample was then calculated:

$$TBA \text{ number} = \frac{1000 \text{ mg}}{S.W.} \times M, (\mu g \text{ malonaldehyde/gram sample})$$

where

S.W. = weight of skin sample collected on the paper strip in mg, M = quantity of malonaldehyde present in 5 ml of aqueous test sample.

The error in this analytic method for determination of malonaldehyde presence, at best, is about ±5%, absolute.

This general procedure afforded several marked experimental advantages. The hardened, ashless filter paper such as used in these experiments has long been recognized as an ideal inert support material for studying lipid peroxidation systems. When skin samples are smeared across the surface of this filter paper, these samples can receive topical application of experimental preparations without subcutaneous absorption losses. Quantification of tests results is then possible. Damage to human skin is avoided, as would occur in some of the following experiments if this procedure was not utilized.

Moistening of the filter paper by capillary action is also an important experimental design, since it simulates the aqueous media present in the epidermis. The skin samples taken and studied by this procedure are actually in contact with air, as is the outer epidermis of the skin. Finally, solar radiation does not pass through a significant liquid phase prior to reaching the skin sample in this experimental design, simulating its passage in reaching the skin surfaces of the body.

The procedure, then, comprises the closest experimental replication of the skin system which is attainable without risking deleterious effects from the formation of carcinogenic agents, yet affording accurate study and control.

In these experiments, all percentages given are weight to volume, unless otherwise indicated.

EXAMPLE I

Demonstration that Skin Lipids Exposed to Sunlight Peroxidize Rapidly with the Evolution of Malonaldehyde Two skin samples were taken and prepared as described in the General Experimental Procedure, parts 1, 2, and 3. A reagent blank consisting of paper strips without a skin sample was also run with the skin samples. Exposure time was 35 minutes.

Weather conditions: sunny day, temperature 80° F. (average temperature during sun exposure as measured in the shade).

The results were as follows:

| Test #/Sample | Sample wt/mg. | Absorb. | TBA No. |
| --- | --- | --- | --- |
| 1. Skin - sun-exposed | 7.5 | 0.138 | 37 |
| Skin - held in dark | 4.3 | 0 | 0 |
| Blank | None | 0 | 0 |
| 2. Skin - sun-exposed | 13.4 | 0.302 | 49 |
| Skin - held in dark | 19.6 | 0.030 | 1 |
| Blank | None | 0 | 0 |

The absence of a TBA number for the blanks indicates that the filter paper and reagents do not interfere with the TBA test. The very low TBA values for skin samples held in the dark indicate that skin lipids neither undergo malonaldehyde formation in the dark nor solely as a result of the experimental design. The high TBA numbers for the sun-exposed samples indicate that ultraviolet radiation is the initiator of rapid malonaldehyde formation on the skin.

Skin lipids thus peroxidize rapidly with the evolution of malonaldehyde when exposed to sunlight, but do not appreciably peroxidize or form malonaldehyde in the dark.

EXAMPLE II

Demonstration that Malonaldehyde Formation from Skin Cannot be Initiated by Elevated Temperature or by a Lengthy Holding Time

Test 1

A sample of skin was taken and prepared as described in the General Experimental Procedure, parts 1 & 2. The cell containing a sample was then placed in a constant temperature box for 75 minutes at 140° F.; part 3 of the Procedure was then completed.

Test 2

A skin sample was taken and prepared as given in the Procedure, parts 1 & 2. The cell was then placed in a dark location for 24 hours at 75° F. Part 3 of the Procedure was then completed.

The results were as follows:

| Test #/Sample | Sample wt. mg. | Absorb. | TBA No. |
| --- | --- | --- | --- |
| 1. Skin held at 140° F., 75 min. | 12.7 | 0.022 | 0 |
| 2. Skin held at 75° F., 24 hrs. | 14.0 | 0.022 | 0 |

Temperatures as high as 115° F. were sometimes recorded in the sun-exposed silica cells described in these experiments. Malonaldehyde formation, however, could not be initiated even at 140° F. in a sealed cell when the skin sample was held in the dark. Also, as Test 2 indicated, a holding time of 24 hours in the dark resulted in negligible malonaldehyde formation.

Sunlight, then, has been identified as the sole initiator of malonaldehyde formation from skin samples.

EXAMPLE III

Demonstration of the Effectiveness of Topically-Applied Sunscreen Preparations for Reducing Malonaldehyde Formation from Skin Samples Exposed to Sunlight The following solutions and emulsions were prepared or obtained:

Solution A—consisted of 5% octyl dimethyl paraaminobenzoate (commercially known as Padimate-O and/or Escalol-507, from Van Dyk & Company, Inc., Belleville, N.J.) in ethanol.

Solution B—consisted of 9% Padimate-O in ethanol.

Solution C—consisted of 33.3% of Coppertone's Tanning Butter (from Plough, Inc., Memphis, Tenn.) in chloroform. Coppertone's Tanning Butter consists of: homosalate, hydrogenated vegetable oil, petrolatum, cocoa butter, cocoanut oil, butyl stearate, paraffin, trihydroxystearin, fragrance, propyl paraben, and butylated hydroxyanisole.

Solution D—consisted of 100% of Coppertone's Suntan Oil (from Plough, Inc., Memphis, Tenn.). Coppertone's Suntan Oil consists of homosalate, mineral oil, lanolin, cocoa butter, propyl paraben, and fragrance.

Emulsion E—consisted of 100% of Osco's Suntan Lotion (from Osco Drug, Inc., Franklin Park, Ill.). Osco's Suntan Lotion consists of: 2-ethoxy-ethyl p-methoxycinnamate, water, stearic acid, glycerol stearate, isopropyl myristate, sesame oil, triethanolamine, cetyl alcohol, perfumes, T.E.A. lauryl sulfate, methyl paraben and propyl paraben.

Emulsion F—consisted of 100% of Coppertone's Super Shade (from Plough, Inc., Memphis, Tenn.). Coppertone's Super Shade contains a mixture of Padimate-O and oxybenzone.

Solution G—consisted of 2% glycerol p-aminobenzoate (Van Dyk & Company, Inc., Belleville, N.J.) in isopropanol.

The following tests were then carried out:

Test 1

Two skin samples were taken as described in the Procedure, part 1, where 50 μl of solution A was applied to one strip and no preparation was applied to the second strip such that it served as a reference. The quantity of solution applied to the sample side of the strip saturated both the skin sample and the filter strip with the preparation, insuring the maximum film thickness of the preparation on the sample.

Parts 2 and 3 of the Procedure were then followed, with a sun exposure time of 90 minutes.

Test 2

Test 1 was repeated, except that one skin sample received 50 μl of solution B, and the other sample was untreated. Sun exposure time was 65 minutes.

Test 3

Test 1 was repeated, except that one skin sample received 150 μl of solution C in three 50 μl increments. The second sample was untreated. Sun exposure time was 120 minutes.

Test 4

Test 1 was repeated, except that one sample received 40 μl of solution D, and the other sample was untreated. Sun exposure time was 120 minutes.

Test 5

Test 1 was repeated except that one sample received 40 μl of emulsion E, and the other sample was untreated. Sun exposure time was 180 minutes.

Test 6

Test 1 was repeated except that one sample received 40 μl of emulsion F, and the other sample was untreated. Sun exposure time was 180 minutes.

Test 7

Test 1 was repeated, except that one sample received 40 μl of solution G, and the other sample was untreated. Sun exposure time was 90 minutes.

| Weather Conditions During Tests | |
|---|---|
| Test # | Weather |
| 1 | Sunny 82° F. |
| 2 | Sunny 90° F. |
| 3 | Sunny 85° F. |
| 4 | Sunny 88° F. |
| 5 | Partly Cloudy 88° F. |
| 6 | Sunny 82° F. |
| 7 | Sunny 75° F. |

The temperatures are average temperatures as measured in the shade.

The following table sets out the results.

| Test #/Sample | Sample wt. mg. | Absorb. | TBA No. | % Reduction of TBA |
|---|---|---|---|---|
| 1 Skin plus Solution A (Padimate-O, 5%) | 7.5 | 0.125 | 33 | +8 |
| Skin Only | 9.2 | 0.162 | 36 | |
| 2 Skin Plus Solution B (Padimate-O, 9%) | 11.4 | 0.185 | 34 | +8 |
| Skin Only | 10.1 | 0.180 | 37 | |
| 3 Skin Plus Solution C (homosalate) | 17.0 | 0.250 | 32 | −6 |
| Skin Only | 9.5 | 0.141 | 30 | |
| 4 Skin Plus Solution D (homosalate) | 11.0 | 0.255 | 50 | −32 |
| Skin Only | 10.2 | 0.183 | 38 | |
| 5 Skin Plus Emulsion E (2-ethyoxy-ethyl p-methoxycinnamate) | 11.7 | 0.190 | 34 | 0 |
| Skin Only | 11.0 | 0.181 | 34 | |
| 6 Skin Plus Emulsion F (Padimate-O plus oxybenzone) | 6.2 | 0.107 | 33 | +51 |
| Skin Only | 5.6 | 0.180 | 67 | |
| 7 Skin Plus Solution G (glycerol p-aminobenzoate) | 10.2 | .315 | 68 | −36 |
| Skin Only | 9.5 | .221 | 50 | −90 |

Solutions A and B contained one of the most effective sunscreens known to the art, octyl dimethyl paraaminobenzoate. In the concentrations used in Test 1 and 2, more than 99% of erythemal radiation was screened from the skin samples. Yet, reduction in TBA number was only slight, about 8%.

Solution C and Emulsion E were regular commercial sunscreen products. These preparations did not markedly effect the TBA number of the skin samples, and are totally ineffective in reducing malonaldehyde formation from skin exposed to sunlight; in fact, application of Solution C resulted in a slight increase in TBA number.

Emulsion F has the highest degree of sunscreen protection commercially available. This preparation containing a mixture of Padimate-O and oxybenzone sunscreens. This combination of sunscreens was capable of reducing malonaldehyde formation by about 51%. Since no other commercial preparation has a higher degree of sunscreen protection than this preparation, TBA reductions greater than 51% appear unachievable with other, weaker, commercial sunscreen systems.

Solution D, containing homosalate (homomenthyl salicylate), caused a significant increase in TBA number; Solution G, containing glycerol-p-aminobenzoate, also caused a significant increase in TBA number. These sunscreens appear to increase the amount of malonaldehyde formed from the skin. This is particularly surprising in the case of Solution G because aminobenzoates are also a nitrogen-containing class of oxidation inhibitor/antioxidant compounds.

These results show that sunscreens, and preparations with sunscreens, vary widely in effectiveness of reducing malonaldehyde formation on the skin during ultraviolet radiation exposure. The most effective commercial sunscreen system only reduces this formation by about 50%. Other systems reduce formation by far less than 50%, and may even enhance malonaldehyde formation.

Use of known commercial sunscreen products thus results in a very significant amount of carcinogenic malonaldehyde being formed on the skin during sun exposure, even when the sunscreen belongs to a nitrogen class of oxidation inhibitor/antioxidant compounds.

EXAMPLE IV

Demonstration of the Effectiveness of Mixtures of Latent Oxidation Inhibitor Compounds and Dermatologically-Acceptable Sunscreens for Reducing Malonaldehyde Formation of Skin Samples Exposed to Sunlight The following solutions and emulsions were prepared:

Solution A.5T

Solution A from Experiment III plus 0.5% Covi-OX T-50 mixed tocopherols (from General Mills Chemicals, Inc., Minneapolis, Minn.) plus 10 ppm BHT. Covi-OX T-50 consists of 50% mixed tocopherols (alpha, beta, gamma, and delta tocopherols) in a vegetable oil.

Solution A2T

Solution A from Experiment III plus 2% Covi-OX T-50 mixed tocopherols and 40 ppm BHT.

Solution A4T

Solution A from Experiment III plus 4% Covi-OX T-50 mixed tocopherols and 80 ppm BHT.

Solution C2T

Solution C from Experiment III plus 2% Covi-OX T-50 mixed tocopherols and 40 ppm BHT.

Solution D2T

Solution D from Experiment III plus 2% Covi-OX T-50 mixed tocopherols and 40 ppm BHT.

Emulsion E2T

Emulsion E from Experiment III plus 2% Covi-OX T-50 mixed tocopherols and 40 ppm BHT.

Emulsion F.5T

Emulsion F from Experiment III plus 0.5% Covi-OX T-50 mixed tocopherols and 10 ppm BHT.

Solution A.5NDGA

Solution A from Experiment III plus 0.5% nordihydroguaiaretic acid (NDGA) (from Aldric Chemical Co., 940 West Saint Paul Ave., Milwaukee, Wisc.).

Solution A.5PG

Solution A from Experiment III plus 0.5 wt % propyl gallate (from Aldric Chemical Co., 940 West Saint Paul Avenue., Milwaukee, Wisc.).

The tocopherols were readily soluble in each of the solutions. They were added to emulsions E and F by heating the emulsions to about 140° F. and then adding the tocopherols to the emulsions with rapid stirring. After cooling the tocopherols were well dispersed in the emulsions. NDGA was soluble in solution A, while propyl gallate was almost entirely soluble in solution a, though a few solids remained even after long stirring.

The following tests were then carried out:

Test 1

Two skin samples were taken as described in the Procedure, part 1, one sample received 50 μl of solution A, and the other sample 50 μl of solution A.5T.

Test 2

Test 1 was repeated, except that three skin samples were taken. One sample received 50 μl of solution A2T, the second sample 50 μl of solution A4T, and the third sample was untreated, so as to serve as a control.

Sun exposure time was 120 minutes.

Test 3

Test 1 was repeated, except that one skin sample received three consecutive applications of 50 μl of solution C from experiment III. The second sample received 150 μl of solution C2T in three consecutive 50 μl applications.

Sun exposure time was 120 minutes.

Test 4

Test 1 was repeated, except that one skin sample received 40 μl of solution D from experiment III, with the second sample receiving 40 μl of solution D2T.

Sun exposure time was 120 minutes.

Test 5

Test 1 was repeated, except that one skin sample received 40 μl of emulsion E from Experiment III, and the second sample received 40 μl of emulsion E2T.

Sun exposure time was 180 minutes.

Test 6

Test 2 was repeated, except that one skin sample received 40 μl of emulsion f, and the second sample received 40 μl of emulsion F.5T. The third sample was untreated.

Sun exposure time was 100 minutes.

Test 7

Test 2 was repeated, except that one sample received 50 μl of solution A.5NDGA and the second 50 μl of solution A.5PG. The third sample received 50 μl of solution a.

Sun exposure time was 180 minutes.

| Weather Conditions During Tests | |
|---|---|
| Test # | Weather Conditions |
| 1 | Sunny 92° F. |
| 2 | Sunny 90° F. |
| 3 | Sunny 85° F. |
| 4 | Sunny 88° F. |
| 5 | Partly Cloudy 88° F. |
| 6 | Sunny 65° F. |
| 7 | Sunny 55° F. |

The following table sets out the results of these tests.

| Test #/Sample | Sample wt. mg. | Absorb. | TBA No. | % Reduction of TBA No. |
|---|---|---|---|---|
| 1 Skin plus solution A (Padimate-O) | 10.2 | 0.110 | 21 | |
| Skin plus Solution A.5T (Padimate-O + tocopherols) | 9.8 | 0.033 | 3 | +86 |
| 2 Skin plus solution A2T (Padimate-O + tocopherols) | 12.6 | 0.043 | 4 | +94 |
| Skin plus solution A4T (Padimate-O + tocopherols) | 10.6 | 0.030 | 2 | +97 |
| Skin Only | 11.5 | 0.337 | 65 | |
| 3 Skin plus solution C (homosalate) | 17.0 | 0.250 | 32 | |

-continued

| Test #/Sample | Sample wt. mg. | Absorb. | TBA No. | % Reduction of TBA No. |
|---|---|---|---|---|
| Skin plus solution C2T (homosalate + tocopherols) | 16.9 | 0.075 | 8 | +75 |
| 4 Skin plus solution D (homosalate) | 11.0 | 0.255 | 50 | |
| Skin plus solution D2T (homosalate + tocopherols) | 14.4 | 0.08 | 10 | +80 |
| 5 Skin plus emulsion E (Cinnamate) | 11.7 | 0.190 | 34 | |
| Skin plus emulsion E2T (Cinnamate + tocopherols) | 13.5 | 0.095 | 13 | +62 |
| 6 Skin plus emulsion F (Padimate-O plus oxybenzone) | 11.1 | 0.095 | 16 | +50 |
| Skin plus emulsion F.5T (Padimate-O plus oxybenzone + tocopherols) | 10.1 | 0.040 | 5 | +84 |
| Skin only | 6.9 | 0.115 | 32 | |
| 7 Skin plus solution A.5NDGA (Padimate-O + NDGA) | 13.5 | .052 | 6 | +77 |
| Skin plus solution A.5PG (Padimate O + propyl gallate) | 13.7 | .050 | 5 | +81 |
| Skin plus solution A | 9.2 | 0.121 | 26 | |

In test 1, solution A.5T reduced malonaldehyde formation from the skin sample 86% more than solution A. The only difference between the solutions is that solution A contains a sunscreen only whereas solution A.5T contains the same sunscreen plus 0.5% stabilized mixed tocopherols.

In test 2 the addition of 2% and 4% stabilized mixed tocopherols to solution A resulted in a 94% and 97% malonaldehyde reduction respectively from the exposed skin samples. This is near total malonaldehyde reduction. However, the use of 4% stabilized tocopherols may cause skin irritation among sensitive individuals.

The commercial suntan products of tests 3, 4 and 5 are shown here to have essentially no effect in reducing malonaldehyde. The addition of 2% stabilized mixed tocopherols improved the performance of these products by 62% to 80%.

Emulsion G, as shown in example III, is the most effective commercial sunscreen system available. This preparation reduces malonaldehyde formation only by about 50%, as again shown in test 6. The addition of 0.5% stabilized mixed tocopherols to this emulsion improves the performance of this product by about 34% for an overall malonaldehyde reduction of 84%.

In test 7, solution A.5NDGA reduced malonaldehyde formation on the skin sample 77% more than solution A. Similarly, solution A.5PG decreased malonaldehyde formation on the skin 81% compared to solution A. Both NDGA and propyl gallate thus are shown to have marked ability to reduce malonaldehyde formation from skin exposed to sunlight.

It is important to note that the commercial sunscreen products of this experiment are not necessarily preferred embodiments of the invention and will not necessarily result in maximum malonaldehyde reduction. Yet, even in these embodiments, the addition of pro-oxidant amounts of latent oxidation inhibitor compounds very significantly improves the performance of commercial sunscreen preparations in reducing malonaldehyde formation. Further note that in tests 1 and 2, which are the optimum compositions of the invention, malonaldehyde reductions of 86 to 97% are effected.

Thus, it is clear that the addition of tocopherols stabilized with BHT in concentrations within the non-sunscreen, pro-oxidant range of 0.1% to 2.0% to preparations with non-tocopherol sunscreens greatly improves the performance of these products in reducing malonaldehyde formation from skin during sun exposure. Similarly, structurally related, non-hindered, non-acid esterified, phenolic substituent-bearing latent oxidation inhibitor compounds such as propyl gallate and NDGA are also effective, although some formulation difficulties were experienced with them because of their more limited oil solubility.

EXAMPLE V

Demonstration of the Effectiveness of Antioxidant-Active Compounds Not Structurally Related to the Tocopherols for Reducing Malonaldehyde Formation from Skin Samples Exposed to Sunlight The following solutions were prepared:

Solution A—0.5BHT

Solution A from Experiment IV was mixed with 0.5% butylated hydroxytoluene.

Solution 1 BHT

One percent (1%) BHT was dissolved in pure cocoanut oil (from Hain Pure Food Co., Inc., Los Angeles, Calif.).

Solution A.5TDPA

Solution A from Experiment IV was mixed with 0.5% thiodipropionic acid.

Solution A—1DLTDP

Solution A from Experiment IV was mixed with 1% dilauryl thiodipropionate.

Solution 1AA

One percent (1%) L-(+)-ascorbic acid in water was neutralized to a pH of 7.3 with sodium hydroxide, so that the ascorbic acid was principally present as its sodium salt.

Solution 1.2 LEC 1.2% lecithin was mixed in ethanol.
The following tests were then carried out:

Test 1

Two skin samples were taken as described in the Procedure, part 1; one sample received 50 μl of solution A-.5BHT and the second sample was untreated.

Parts 2 and 3 of the Procedure were then followed with a sun exposure time of 90 minutes.

Test 2

Test 1 was repeated, except that one skin sample received 50 μl of solution 1 BHT and the second sample was untreated.

Sun exposure time was 260 minutes.

Test 3

Test 1 was repeated, except that one skin sample received 50 μl of solution A—0.5TDPA and the second sample was untreated.

Sun exposure time was 90 minutes.

Test 4

Test 1 was repeated, except that one skin sample received 50 μl of solution 1AA and the second sample was untreated.

Sun exposure time was 145 minutes.

Test 5

Test 1 was repeated, except that one skin sample received 50 μl of solution A-1 DLTDP and the second sample was untreated.

Sun exposure time was 120 minutes.

Test 6

Test 1 was repeated, except that one skin sample received 50 μl of solution 1.2 LEC and the second sample was untreated.

Sun exposure time was 90 minutes.

Test 7

Test 1 was repeated, except that one skin sample received 150 μl of solution C from Experiment III in three 50 μl increments, and the second sample was untreated.

Sun exposure time was 120 minutes.

| Weather Conditions During Tests | |
|---|---|
| Test # | Weather Conditions |
| 1 | Sunny 85° F. |
| 2 | Partly Cloudy 75° F. |
| 3 | Sunny 85° F. |
| 4 | Sunny 65° F. |
| 5 | Sunny 45° F. |
| 6 | Sunny 55° F. |
| 7 | Sunny 85° F. |

The results are set out in the following table.

| Test #/Sample | Sample wt. mg. | Absorb. | TBA No. | % Reduct. of TBA No. |
|---|---|---|---|---|
| 1 Skin plus solution A-.5BHT | 10.5 | 0.135 | 26 | +26 |
| Skin Only | 11.6 | 0.195 | 35 | |
| 2 Skin plus solution 1 BHT | 11.3 | 0.142 | 25 | +26 |
| Skin Only | 10.2 | 0.172 | 35 | |
| 3 Skin plus solution A-.5TDPA | 11.6 | 0.195 | 35 | 0 |
| Skin Only | 11.6 | 0.195 | 35 | |
| 4 Skin plus solution 1AA | 7.0 | 0.090 | 23 | +41 |
| Skin Only | 6.9 | 0.135 | 39 | |
| 5 Skin plus solution A-1 DLTDP | 7.5 | .073 | 17 | +23 |
| Skin Only | 6.4 | .080 | 22 | |
| 6 Skin plus solution 1.2 LEC | 12.1 | 0.150 | 25 | −9 |
| Skin Only | 10.6 | 0.123 | 23 | |
| 7 Skin plus solution C | 17.0 | 0.25 | 32 | −7 |
| Skin Only | 9.5 | 0.141 | 30 | |

The antioxidant-active compounds testes in this experiment are food antioxidants representing several different classes of compounds: BHT and BHA are examples of hindered phenols, thiodipropionic acid and dilauryl thiodipropionate are examples of sulfur types of antioxidants, and lecithin is a phospholipid-type antioxidant. Yet each one failed to meet one or more of the criteria necessary for an effective compound of this invention, i.e., a non-hindered, non-acid esterified, oil soluble, phenolic substituent-bearing compound. As such, they were relatively ineffective in reducing malonaldehyde formation on skin samples during exposure to solar radiation.

These oil soluble antioxidants were tested in concentrations ranging from about 10 to 50 times greater than their maximum permitted concentration in foods. Yet, even at these high concentrations, combined with an ultraviolet absorbing sunscreen compound, ineffective performance resulted: solution C is a commercial suntan product containing a sunscreen (homosalate) and antioxidant (BHA), but this preparation was wholly ineffective in reducing malonaldehyde.

Ascorbic acid reduced malonaldehyde concentration from the sample by 41%. Ascorbic acid and its salts are not oil soluble, so absorbic acid did not prevent malonaldehyde formation; rather, since ascorbic acid is a powerful water soluble-reducing agent, it probably reduced water soluble malonaldehyde to an alcohol compound after its formation. It appears that ascorbic acid does not prevent malonaldehyde formation, then, and is only moderately active in reducing malonaldehyde after its formation on the skin.

This experiment thus shows that effective food antioxidants which are hindered, or non-phenolic, or acid esterified are essentially ineffective in reducing malonaldehyde formation even when used in concentrations up to 50 times greater than the art teaches as their normal antioxidant range. It further shows that ascorbic acid also does not prevent malonaldehyde formation from skin lipids but has relatively modest activity in reducing malonaldehyde after it is found on the skin. This property of ascorbates is important, however, because ascorbates are well known tocopherol synergists, the tocopherols being particularly efficacious in the compositions of this invention.

EXAMPLE VI

Demonstration of the Lack of Effectiveness of Hydroquinone in Oily Vehicles for Malonaldehyde Reduction from Sun-Exposed Skin Two solutions were prepared:

Solution U consisted of a light mineral oil that was saturated with hydroquinone.

Solution V consisted of pure corn oil that was saturated with hydroquinone.

Two samples of skin were obtained, and one received 40 μl of Solution U and the other 40 μl of Solution V. The samples were sun exposed 120 minutes along with a reference skin sample as described in the General Experimental Procedure.

Weather Conditions: Sunny, 80° F.

The results are set out in the following table.

| Test #/Sample | Sample wt. mg. | Absorb. | TBA No. | % Reduct. of TBA Number |
|---|---|---|---|---|
| Skin plus Solution U | 8.5 | .13 | 30 | +13% |
| Skin plus Solution V | 9.1 | .14 | 31 | +12% |
| Skin Only | 9.3 | .16 | 35 | |

Both mineral oil and vegetable oil saturated with hydroquinone were essentially ineffective in reducing malonaldehyde formation from skin samples exposed to sunlight.

Although hydroquinone is a non-hindered, non-acid esterified phenolic-type oxidation inhibitor compound, its poor oil solubility renders it useless for the purpose of this invention.

EXAMPLE VII

Demonstration that Acid Esterification of Latent Oxidation Inhibitor Compounds Destroys Their Effectiveness in Reducing Malonaldehyde Formation on Sun-Exposed Skin A sample of d-alpha tocopherol acetate (from K-Mart Corporation, Troy, Mich.) was obtained. This preparation contained 50% (wt/wt) of the acid ester of alpha tocopherol in an oil. A solution consisting of 2% d-alpha tocopherol acetate and 5% Padimate-O in ethanol was prepared and labeled "Solution A-acid ester."

Three skin samples were obtained as described in the Procedure. One skin sample received a 50 μl application of Solution A-acid ester. The other sample received 50 μl of Solution A2T from Experiment IV. The third sample served as a reference or control.

The samples were then tested as described in parts 2-3 of the Procedure with a sun-exposure time of 105 minutes.

Weather conditions: Sunny, 85° F.

The results are set out in the following table:

| Test #/Sample | Sample wt. mg. | Absorb. | TBA No. | % Reduction of TBA No. |
|---|---|---|---|---|
| Skin plus Solution A-acid ester | 8.5 | 0.197 | 49 | 8 |
| Skin plus Solution A2T | 8.9 | 0.048 | 7 | 86 |
| Skin Only | 9.2 | 0.226 | 53 | |

It is well known in the antioxidant arts that destruction of the functional hydroxy (—OH) group by acid esterification destroys the antioxidant properties of an antioxidant-active compound. In this experiment it is also shown that acid esterification destroys the malonaldehyde-reducing effectiveness of latent oxidation inhibitor compounds when used in topically-applied cosmetic preparations. The free tocopherol was 1,075% more effective than the acid ester in reducing malonaldehyde formation on the skin during sun exposure in this experiment.

Acid esterification of latent oxidation inhibitor compounds thus destroys their effectiveness for reducing malonaldehyde formation from skin exposed to sunlight.

EXAMPLE VIII

Demonstrate the Lower Useful Concentration Range of Latent Oxidation Inhibitor Compounds and Sunscreen Mixtures for Reducing Ultraviolet-Induced Malonaldehyde Formation on Skin

Test 1

Four solutions were prepared: Solution A consisted of 5% Padimate-O in ethanol, and, to Solution A, 0.1%, 0.05%, and 0.01% alpha tocopherol were added and labeled A.1, A..05, A.01, respectively.

Four samples of skin were taken as described in the Procedure, part 1. Three samples received 50 μl of either solution A.1, A.05 or A.01. The fourth sample was a skin sample only, serving as a control.

Fifteen minutes were allowed to pass before the samples were exposed to the sun. This delay to exposure is important, as it allows time for the tocopherols to diffuse from the preparation to the skin; if sufficient time for diffusion is not allowed prior to exposure to ultraviolet radiation, the effectiveness of the preparation is decreased. Then parts 2 and 3 of the Procedure were performed after a sun exposure time of 120 minutes.

Weather conditions: Sunny, 62° F.

Test 2

Four solutions were prepared: Solution M consisted of 5% Padimate-O in white mineral oil (liquid petrolatum), and, to solution M, 0.2%, 0.1%, and 0.05% Covi-OX T-50 mixed tocopherols and 5, 2 and 0.01 ppm BHT, were added and labeled M.2, M.1, and M.05, respectively.

Three samples of skin were taken as described in the Procedure, part 1. The skin samples received 40 μl of either solution M.2, M.1 or M.05.

Fifteen minutes were allowed to pass before sun exposure. Then parts 2 and 3 of the Procedure were performed after a sun-exposure time of 2 hours.

Weather conditions: Sunny, 62° F.

Test 3

To solution A was added 0.05% and 0.1% propyl gallate; the solutions were labeled A.05PG and A.1PG, respectively.

The sun-exposure test was then run as described in Test 1, except exposure time was 2½ hours.

Weather conditions: Sunny, 60° F.

Test 4

To Solution A was added 0.05% and 0.1% NDGA; these solutions were labeled A.05 NDGA, and A.1 NDGA, respectively.

The sun-exposure test was then run as described in Test 1, except sun exposure was 2½ hours.

Weather conditions: Sunny, 60° F.

Test 5

To Solution M was added 0.03% propyl gallate, and to a second portion 0.3% NDGA; these solutions were labeled M.3PG and M.3NDGA, respectively.

Test 6

Solution A.0.5PG—0.05T was prepared by adding to Solution a 0.05% propyl gallate and 0.05% mixed tocopherols.

Solution A.05T—0.05PG—0.05NDGA was prepared by adding to Solution A 0.05% mixed tocopherols, 0.05% propyl gallate, and 0.05% NDGA.

The sun-exposure test was then run as described in Test 1 on these two solutions, except sun-exposure time was 2½ hours.

Weather conditions: Sunny, 55° F.

| Test #/Sample | Sample wt. mg. | Absorb. | TBA No. | % Reduction of TBA No. |
|---|---|---|---|---|
| 1 Skin plus Solution A-0.1T | 8.3 | 0.065 | 13 | 65 |
| Skin plus Solution A-0.05T | 11.0 | 0.135 | 25 | 34 |
| Skin plus Solution A-0.01T | 9.4 | 0.152 | 33 | 11 |
| Skin Only | 8.6 | 0.155 | 37 | |
| 2 Skin plus Solution M-0.2T | 10.0 | 0.053 | 8 | 78 |
| Skin plus Solution M-0.1 | 8.6 | 0.077 | 16 | 56 |
| Skin plus Solton M-0.05T | 8.2 | 0.109 | 25 | 31 |
| Skin Only | 9.3 | .163 | 36 | |
| 3 Skin plus Solution A-0.1PG | 8.4 | .078 | 16 | 55 |
| Skin plus Solution A0.05PG | 6.3 | .075 | 20 | 43 |
| Skin Only | 8.3 | 0.147 | 36 | |
| 4 Skin plus Solution A0.1 NDGA | 8.6 | 0.06 | 11 | 69 |
| Skin plus Solution A-0.05 NDGA | 7.5 | 0.078 | 18 | 48 |
| Skin Only | 9.4 | 0.160 | 35 | |
| 5 Skin plus Solution M-0.3PG | 9.0 | 0.063 | 11 | 70 |
| Skin plus Soluton M-0.3 NDGA | 9.4 | 0.107 | 22 | 43 |
| Skin Only | 9.4 | 0.172 | 38 | |
| 6 Skin plus Solution A.05PG-.05T | 8.4 | 0.035 | 4 | 88 |
| Skin plus Solution A-.05PG-.05T NDGA | 11.0 | 0.038 | 4 | 89 |
| Skin Only | 8.6 | 0.148 | 35 | |

A linear regression curve was calculated for the Test 1 and Test 2 data by the least squares method. From these equations, the lower maximum effective limit for tocopherols in an evaporative carrier vehicle such as alcohol was calculated to be 0.16%. The lower maximum limit for a non-evaporative carrier vehicle such as petrolatum was calculated to be 0.265%. These concentrations, which are based on total composition weight, correspond to nearly complete malonaldehyde reduction.

As shown by tests 3, 4 and 5, acceptable malonaldehyde reduction occurred for propyl gallated and NDGA-containing protective compositions with an evaporative base when the antioxidant concentration was about 0.1%. When used in a petrolatum-based composition, a concentration of about 0.3% propyl gallate yielded satisfactory results, but 0.3% NDGA was relatively ineffective. 0.3% is near or at the solubility limit for both NDGA and propyl gallate in petrolatum, so improvement in performance by increasing the concentration of these antioxidants is not possible, particularly as any such increase will cause skin irritation, as the amounts present in excess of the solubility limit will be directly present on the skin.

Mixtures of tocopherols and either propyl gallate of NDGA were effective, as shown in test 6, provided their combined concentration were about 0.1 to 0.15%.

These tests also show that the lower concentration limit of latent oxidation inhibitor compounds for acceptable reduction of solar malonaldehyde formation on the skin was equal to about 0.1% for alcoholic-based preparations and and about 0.2% for petrolatum-based preparations, whether such compounds were used alone or in mixtures, except for NDGA, which seems relatively ineffective in a mineral oil-type vehicle. Since alcoholic and lotion-type preparations will contain a minimum of about 5 and a maximum of about 50 wt % of a fatty or oily component, the lower acceptable concentration limit of the latent oxidation inhibitor compounds will range from about 0.2 to 2 wt % relative to the fat and oil content of the preparation. For preparations which are entirely oil or fat-based, said lower acceptable limit will be about 0.2 wt % relative to the fat or oil content of the preparation.

Neither propyl gallate nor NDGA had outstanding performance in petrolatum-based preparations even when present at their saturation concentration. Combinations of inhibitor compounds seemed particularly effective, and overcame the problems with the limited oil solubilities of the non-tocopherol latent oxidation inhibitor compounds.

Since these lower limit concentrations are not necessarily the optimum concentration, both propyl gallate and NDGA will be less effective than tocopherols in oil-based preparations, because of solubility problems. Also, both NDGA and propyl gallate will form ineffective crystals on the skin when used in optimum concentrations in evaporative-based preparations containing oily sunscreens. These undissolved crystals will also add to irritation and sensitization of the skin.

Tocopherols do not demonstrate these shortcomings at any concentration in any type of base.

EXAMPLE IX

Demonstration of Preferred Protective Compositions of the Invention

A protective composition consisting of 4% Padimate-O, 0.2% Covi-OX T-50 mixed tocopherols, 0.02% BHT, and 0.1% ascorbic acid in ethanol was prepared. This solution was labeled "solution Y" and contained 0.2% mixed tocopherols.

A second protective composition consisting of 0.2% Covi-OX T-50 mixed tocopherols, 0.02% BHT, 0.1% disodium EDTA, in Coppertone's Super Shade was prepared and labeled "emulsion 2." Emulsion 2 contained 0.2% mixed tocopherols. Three skin samples were taken as described in the Procedure, part 1. Fifty $\mu$l of solution Y was spread evenly on one sample, and 50 $\mu$l of emulsion 2 was spread evenly on the second sample. The third sample was untreated as a control.

After waiting 15 minutes, parts 2 and 3 of the Procedure were performed with a sun exposure time of 120 minutes.

Weather conditions: Sunny, 72° F.

| Sample | Sample wt. mg. | Absorb. | TBA No. | % Reduction of TBA No. |
|---|---|---|---|---|
| Skin plus solution Y | 9.6 | 0.037 | 4 | 90 |
| Skin plus emulsion 2 | 14.9 | 0.042 | 4 | 90 |
| Skin Only | 6.6 | 0.137 | 42 | |

The preferred protective compositions of the invention, as this data shows, will contain an oil soluble latent oxidation inhibitor stabilizer—synergist, such as BHT and BHA. When a tocopherol is present in an alcohol or emulsion protective composition, an alcohol or water soluble synergist such as an ascorbate or metal chelating agent such as disodium EDTA should be present along with the oil soluble tocopherol synergist. An alkylated ester of p-aminobenzoic acid such as Padimate-O is here shown to be the optimum oil and alcohol soluble ultraviolet absorbing sunscreen compound for use in the protective combination of the invention.

EXAMPLE X

Demonstration of an In Vivo Malonaldehyde Reduction by Topical Application of a Tocopherol-Containing Composition

Procedure

A solution consisting of 5% Padimate-O, 2% Covi-OX T-50 mixed tocopherols and 80 PPM BHT in ethanol was prepared and identified as solution I. This solution contained 2% mixed tocopherols. A second solution consisting of 5% Padimate-O and 0.5% BHT in ethanol was prepared and identified as solution II.

An application of solution I was made on one-half of the face of the subject; then an equal application of solution II was made on the second half of the subject's fact. Fifteen minutes passed before sun exposure of the face. At this time it appeared that both solution I and II had penetrated the skin well, since neither solution could be seen on the face. The face was exposed to sunlight for 45 minutes.

Marked facial perspiration occurred during the exposure period.

Immediately after exposure, samples were taken from the face as described in the Procedure, part 1. The samples contained much visible perspiration. After completing part 3 of the Procedure, the following results were obtained:

| Sample No. | Sample Wt. mg. | Absorb. | TBA No. | % Reduct. of TBA No. |
|---|---|---|---|---|
| 1. ½ of face w/solution I | 46.6 | .035 | 0.75 | 76.6 |
| 2. ½ of face w/solution II | 47.0 | .085 | 3.2 | |

The results of this test are semi-quantitative because of the large and uncontrollable amounts of perspiration that formed on the face during the test. Yet, the direction of the test data is clear: topically-applied, stabilized tocopherols, in amounts that are less than the minimum sunscreen-effective amount, combined with an effective sunscreen, greatly reduced malonaldehyde formation on living skin exposed to sunlight. The concentration of tocopherols used in this test screened less than 50% of the incident solar erythmal light from the face.

This in vivo experiment confirms the findings of the in vivo tests previously described.

While particular embodiments of the invention have been shown, it will be understood, of course, that the invention is not limited thereto since modifications may be made by those skilled in the art, particularly in light of the foregoing teachings. It is, therefore, contemplated by the appended claims to cover any such modifications as incorporate those features which constitute the essential features of these improvements within the true spirit and the scope of the invention.

I claim:

1. A method of preventing the solar radiation absorption-induced formation of skin lipid degradation products, particularly malonaldehyde, consisting of the external application of a protective composition which substantially prevents said degradation product formation, prior to exposure of the skin to natural or artificial sources of solar radiation, said composition comprising:

an ultraviolet screen-effective amount of an ultraviolet absorbing compound selected from the group consisting of a salicylate, a para-aminobenzoate, an alkyl ester of para-dialkylaminobenzoic acid, a benzophenone, a cinnamate, a naphthoate, an acid-esterified gallate, and mixtures thereof;

at least one non-hindered, non-acid esterified, oil soluble phenolic substituent-bearing latent oxidation inhibitor compound, the total concentration of said inhibitor present constituting a pro-oxidant effective amount of no less than about 0.2% by weight of the total fat and oil content of said total composition, said inhibitor concentration further constituting an amount less than 2 weight percent of said total composition, said amount being insufficient to constitute an ultraviolet screen-effective amount demonstrating absorption of at least 85% of incident ultraviolet radiation; and at least about 5% by weight of an inert carrier vehicle for said compounds comprising a fat or oil component, said vehicle being non-toxic and non-irritating to the skin.

2. The method according to claim 1 wherein said phenolic substituent-bearing latent oxidation inhibitor compound is selected from the group consisting of alpha tocopherol, beta tocopherol, gamma tocopherol, delta tocopherol, epsilon tocopherol, zeta tocopherol, eta tocopherol, alcoholic esters of gallic acid, nordihydroguaiaretic acid, and mixtures thereof.

3. The method according to claim 1 wherein said oil of fat component of said carrier vehicle is selected from the group consisting of mineral oil, vegetable oil, petrolatum, silicone oil, oily sunscreen, waxes and mixtures thereof, said composition containing at least about 5% by weight of said component.

4. The method according to claim 2 wherein said oil or fat component of said carrier vehicle is selected from the group consisting of mineral oil, vegetable oil, petrolatum, silicone oil, oily sunscreen, waxes and mixtures thereof, said composition containing at least about 5% by weight of said component.

5. The method according to claim 1 wherein said ultraviolet absorbing compound of said composition is an alkyl ester of para-dialkylaminobenzoic acid.

6. The method according to claim 2 wherein said ultraviolet absorbing compound of said composition is an alkyl ester of para-dialkylaminobenzoic acid.

7. The method according to claim 3 wherein said ultraviolet absorbing compound of said composition is an alkyl ester of para-dialkylaminobenzoic acid.

8. The method according to claim 2 wherein said composition additionally comprises a tocopherol synergist compound.

9. The method according to claim 4 wherein said composition additionally comprises a tocopherol synergist compound.

10. The method according to claim 6 wherein said composition additionally comprises a tocopherol synergist compound.

11. The method according to claim 7 wherein said composition additionally comprises a tocopherol synergist compound.

12. The method according to claim 8 wherein said tocopherol synergist compound is selected from the group consisting of butylated hydroxytoluene, butylated hydroxyanisole, ascorbic acid, an ascorbic acid salt, an ascorbic acid ester, citric acid, a critic acid salt, a citric acid ester, a phosphoric acid salt, a phosphoric acid ester and mixtures thereof.

13. A method of preventing the solar radiation absorption-induced formation of skin lipid degradation products, particularly malonaldehyde, consisting of the external application of a protective composition which substantially prevents said degradation product formation, prior to exposure of the skin to natural or artificial sources of solar radiation, said composition comprising:
an ultraviolet screen-effective amount of an oil soluble, ultraviolet absorbing compound selected from the group consisting of a salicylate, a para-aminobenzoate, an alkyl ester of para-dialkylaminobenzoic acid, a benzophenone, a cinnamate, a naphthoate, an acid-esterified gallate, an mixtures thereof; and
at least one non-hindered, non-acid esterified, oil soluble phenolic substituent-bearing latent oxidation inhibitor compound, the total concentration of said inhibitor present constituting a pro-oxidant effective amount of no less than about 0.2% by weight of the total fat and oil content of said total composition, said inhibitor concentration further constituting an amount less than 2 weight percent of said total composition, said amount being insufficient to constitute an ultraviolet screen-effective amount demonstrating absorption of at least 85% of incident ultraviolet radiation.

14. The method according to claim 13 wherein said phenolic substituent-bearing latent oxidation inhibitor compound is selected from the group consisting of alpha tocopherol, beta tocopherol, gamma tocopherol, delta tocopherol, epsilon tocopherol, zeta tocopherol, eta tocopherol, alcoholic esters of gallic acid, nordihydroguaiaretic acid and mixtures thereof.

15. The method according to claim 13 wherein said ultraviolet absorbing compound of said composition is an alkyl ester of para-dialkylaminobenzoic acid.

16. The method according to claim 14 wherein said ultraviolet absorbing compound of said composition is an alkyl ester of para-dialkylaminobenzoic acid.

17. The method according to claim 13 wherein said composition additionally comprises a tocopherol synergist compound.

18. The method according to claim 14 wherein said composition additionally comprises a tocopherol synergist compound.

19. The method according to claim 17 wherein said tocopherol synergist compound is selected from the group consisting of butylated hydroxytoluene, butylated hydroxyanisole, ascorbic acid, an ascorbic acid salt, an ascorbic acid ester, citric acid, a citric acid salt, a citric acid ester, a phosphoric acid salt, a phosphoric acid ester and mixtures thereof.

20. A method of preventing the solar radiation absorption-induced formation of skin lipid degradation products, particularly malonaldehyde, consisting of the external application of a protective composition which substantially prevents said degradation product formation, prior to exposure of the skin to natural or artificial sources of solar radiation, said composition comprising:
an ultraviolet screen-effective amount of an ultraviolet absorbing compound selected from the group consisting of a salicylate, a para-aminobenzoate, an alkyl ester of para-dialkylaminobenzoic acid, a benzophenone, a cinnamate, a naphthoate, an acid-esterified gallate, and mixtures thereof;
at least one non-hindered, non-acid esterified, oil soluble phenolic substituent-bearing latent oxidation inhibitor compound, the total concentration of said inhibitor present constituting a pro-oxidant effective amount of no less than about 0.2% by weight of the total fat and oil content of said total composition, said inhibitor concentration further constituting an amount less than 2 weight percent of said total composition, said amount being insufficient to constitute an ultraviolet screen-effective amount demonstrating absorption of at least 85% of incident ultraviolet radiation; and
at least about 5% by weight of an inert carrier vehicle for said compounds comprising a fat or oil component, and an evaporative component, said vehicle being non-toxic and non-irritating to the skin.

21. A solar radiation skin lipid degradation-preventing protective composition for external application to the skin comprising:
an ultraviolet screen-effective amount of an ultraviolet absorbing compound selected from the group consisting of a salicylate, a para-aminobenzoate, an alkyl ester of para-dialkylaminobenzoic acid, a benzophenone, a cinnamate, a naphthoate, an acid-esterified gallate, and mixtures thereof;
at least one non-hindered, non-acid esterified, oil soluble phenolic substituent-bearing latent oxidation inhibitor compound, the total concentration of said inhibitor present constituting a pro-oxidant effective amount of no less than about 0.2% by weight of the total fat and oil content of said total composition, said inhibitor concentration further constituting an amount less than 2 weight percent of said total composition, said amount being insufficient to constitute an ultraviolet screen-effective amount demonstrating absorption of at least 85% of incident ultraviolet radiation; and at least about 5% by weight of an inert carrier vehicle for said compounds comprising a fat or oil component, said vehicle being non-toxic and non-irritating to the skin.

22. The composition according to claim 21 wherein said phenolic substituent-bearing latent oxidation inhibitor compound is selected from the group consisting of alpha tocopherol, beta tocopherol, gamma tocopherol, delta tocopherol, epsilon tocopherol, zeta tocopherol, eta tocopherol, alcoholic esters of gallic acid, nordihydroguaiaretic acid and mixtures thereof.

23. The composition according to claim 21 wherein said oil or fat compound of said carrier vehicle is selected from the group consisting of mineral oil, vegetable oil, petrolatum, silicone oil, oily sunscreen, waxes and mixtures thereof, said composition containing at least about 5% by weight of said component.

24. The composition according to claim 21 wherein said ultraviolet absorbing compound of said composition is an alkyl ester of para-dialkylaminobenzoic acid.

25. The composition according to claim 22 wherein said ultraviolet absorbing compound of said composition is an alkyl ester of para-dialkylaminobenzoic acid.

26. The composition according to claim 23 wherein said ultraviolet absorbing compound of said composition is an alkyl ester of para-dialkylaminobenzoic acid.

27. The composition according to claim 22 wherein said composition additionally comprise a tocopherol synergist compound.

28. The composition according to claim 23 wherein said composition additionally comprises a tocopherol synergist compound.

29. The composition according to claim 25 wherein said composition additionally comprises a tocopherol synergist compound.

30. The composition according to claim 27 wherein said tocopherol synergist compound is selected from the group consisting of butylated hydroxytoluene, butylated hydroxyanisole, ascorbic acid, an ascorbic acid salt, an ascorbic acid ester, citric acid, a citric acid salt, a citric acid ester, a phosphoric acid salt, a phosphoric acid ester and mixtures thereof.

31. A solar radiation skin lipid degradation-preventing protective composition for external application to the skin comprising:

an ultraviolet screen-effective amount of an ultraviolet absorbing compound selected from the group consisting of a salicylate, a para-aminobenzoate, an alkyl ester of para-dialkylaminobenzoic acid, a benzophenone, a cinnamate, a naphthoate, an acid-esterified gallate, and mixtures thereof; and at least one non-hindered, non-acid esterified, oil soluble phenolic substituent-bearing latent oxidation inhibitor compound, the total concentration of said inhibitor present constituting a pro-oxidant effective amount of no less than about 0.2% by weight of the total fat and oil content of said total composition, said inhibitor concentration further constituting an amount less than 2 weight percent of said total composition, said amount being insufficient to constitute an ultraviolet screen-effective amount demonstrating absorption of at least 85% of incident ultraviolet radiation.

32. The composition according to claim 31 wherein said phenolic substituent-bearing latent oxidation inhibitor compound is selected from the group consisting of alpha tocopherol, beta tocopherol, gamma tocopherol, delta tocopherol, epsilon tocopherol, zeta tocopherol, eta tocopherol, alcoholic esters of gallic acid, nordihydroguaiaretic acid and mixtures thereof.

33. The composition according to claim 31 wherein said ultraviolet absorbing compound of said composition is an alkyl ester of para-dialkylaminobenzoic acid.

34. The composition according to claim 32 wherein said ultraviolet absorbing compound of said composition is an alkyl ester of para-dialkylaminobenzoic acid.

35. The composition according to claim 31 wherein said composition additionally comprises a tocopherol synergist compound.

36. The composition according to claim 32 wherein said composition additionally comprises a tocopherol synergist compound.

37. The composition according to claim 35 wherein said tocopherol synergist compound is selected from the group consisting of butylated hydroxytoluene, butylated hydroxyanisole, ascorbic acid, an ascorbic acid salt, an ascorbic acid ester, citric acid, a citric acid salt, a citric acid ester, a phosphoric acid salt, a phosphoric acid ester and mixtures thereof.

38. A solar radiation skin lipid degradation-preventing protective composition for external application to the skin comprising:

an ultraviolet screen-effective amount of an ultraviolet absorbing compound selected from the group consisting of a salicylate, a para-aminobenzoate, an alkyl ester of para-dialkylaminobenzoic acid, a benzophenone, a cinnamate, a naphthoate, an acid-esterified gallate, and mixtures thereof;

at least one non-hindered, non-acid esterified, oil soluble phenolic substituent-bearing latent oxidation inhibitor compound, the total concentration of said inhibitor present constituting a pro-oxidant effective amount of no less than about 0.2% by weight of the total fat and oil content of said total composition, said inhibitor concentration further constituting an amount less than 2 weight percent of said total composition, said amount being insufficient to constitute an ultraviolet screen-effective amount demonstrating absorption of at least 85% of incident ultraviolet radiation; and at least about 5% by weight of an inert carrier vehicle for said compounds comprising a fat or oil component, and an evaporative component, said vehicle being non-toxic and non-irritating to the skin.

* * * * *

UNITED STATES PATENT AND TRADEMARK OFFICE
CERTIFICATE OF CORRECTION

PATENT NO. : 4,975,272

DATED : December 4, 1990

INVENTOR(S) : Walter F. Voyt

It is certified that error appears in the above-identified patent and that said Letters Patent is hereby corrected as shown below:

Column 9, line 60, "Perspiration" should be -- perspriation --

Column 11, line 13, after "vehicle" insert a period (.)

Column 12, line 24, "0 2" should be -- 0.2 -- line 36, "t" should be -- to --

Column 15, line 8, "Paper" should be -- paper -- line 9, "Paper" should be -- paper -- line 10, "Paper" should be -- paper --

Column 29, in the second to the last line of the table, "A.05PG-.05T NDGA" should be -- A - .05T-.05PG-.05 NDGA --

UNITED STATES PATENT AND TRADEMARK OFFICE
CERTIFICATE OF CORRECTION

PATENT NO. : 4,975,272

DATED : December 4, 1990

INVENTOR(S) : Walter F. Voyt

It is certified that error appears in the above-identified patent and that said Letters Patent is hereby corrected as shown below:

Column 32, line 21, "in vivo" should be -- in vitro -- line 22, "in vivo" should be -- in vitro --

Signed and Sealed this

Twenty-first Day of July, 1992

Attest:

DOUGLAS B. COMER

Attesting Officer

Acting Commissioner of Patents and Trademarks